(12) United States Patent
Nojiri et al.

(10) Patent No.: US 11,531,013 B2
(45) Date of Patent: Dec. 20, 2022

(54) GAS SENSOR, GAS DETECTION DEVICE, GAS DETECTION METHOD, AND DEVICE PROVIDED WITH GAS SENSOR OR GAS DETECTION DEVICE

(71) Applicant: SEMITEC Corporation, Tokyo (JP)

(72) Inventors: Toshiyuki Nojiri, Tokyo (JP); Dezhi Cheng, Tokyo (JP)

(73) Assignee: SEMITEC Corporation, Tokyo (JP)

( * ) Notice: Subject to any disclaimer, the term of this patent is extended or adjusted under 35 U.S.C. 154(b) by 288 days.

(21) Appl. No.: 16/636,909

(22) PCT Filed: Jul. 26, 2018

(86) PCT No.: PCT/JP2018/028058
§ 371 (c)(1),
(2) Date: Feb. 6, 2020

(87) PCT Pub. No.: WO2019/031260
PCT Pub. Date: Feb. 14, 2019

(65) Prior Publication Data
US 2020/0166493 A1    May 28, 2020

(30) Foreign Application Priority Data

Aug. 9, 2017   (JP) .............................. JP2017-154003

(51) Int. Cl.
*G01N 33/00*   (2006.01)
*G01K 7/22*   (2006.01)
(Continued)

(52) U.S. Cl.
CPC ........... *G01N 33/0016* (2013.01); *G01K 7/22* (2013.01); *G01K 7/223* (2013.01); *G01N 27/12* (2013.01);
(Continued)

(58) Field of Classification Search
CPC .. G01N 33/0016; G01N 27/12; G01N 27/121; G01N 27/123; G01N 27/125; G01N 27/14; G01K 7/22; G01K 7/223
See application file for complete search history.

(56) References Cited

U.S. PATENT DOCUMENTS 4,080,564 A * 3/1978 Nitta .................... G01N 27/121
                                                         324/696
4,397,888 A * 8/1983 Yannopoulos ......... G01N 27/12
                                                         427/376.6
(Continued)

FOREIGN PATENT DOCUMENTS

CN           1298100        6/2001
CN          102192792       9/2011
(Continued)

OTHER PUBLICATIONS

"International Search Report (Form PCT/ISA/210) of PCT/JP2018/028058," dated Sep. 25, 2018, with English translation thereof, pp. 1-4.
(Continued)

*Primary Examiner* — Benjamin R Schmitt
(74) *Attorney, Agent, or Firm* — JCIPRNET

(57) ABSTRACT

Provided are: a gas sensor which is able to have improved gas detection performance, while being capable of suppressing variation in the output characteristics among individual gas sensors; a gas detection device; a gas detection method; and a device which is provided with a gas sensor or a gas detection device. This gas detection device (10) is provided with: a heat sensitive resistive element (2); a lead part (22b) which is connected to the heat sensitive resistive element (2) by welding, while having no material being interposed therebetween; a gas sensor (1) which is thermally coupled to the heat sensitive resistive element (2), while comprising a porous gas molecule adsorption material (3) from which
(Continued)

specific gas molecules are desorbed by means of heating; and an electric power supply unit which supplies electric power to the heat sensitive resistive element (2), thereby heating the heat sensitive resistive element (2).

17 Claims, 7 Drawing Sheets

(51) Int. Cl.
*G01N 27/12* (2006.01)
*G01N 27/14* (2006.01)

(52) U.S. Cl.
CPC ......... *G01N 27/121* (2013.01); *G01N 27/123* (2013.01); *G01N 27/125* (2013.01); *G01N 27/14* (2013.01)

(56) References Cited

U.S. PATENT DOCUMENTS

| | | | |
|---|---|---|---|
| 2003/0039299 A1* | 2/2003 | Horovitz | G01N 27/16 374/31 |
| 2004/0194546 A1* | 10/2004 | Kanehori | G01N 27/225 29/595 |
| 2008/0295590 A1* | 12/2008 | Sukegawa | G01F 1/6983 73/204.26 |

FOREIGN PATENT DOCUMENTS

| | | |
|---|---|---|
| CN | 104422712 | 3/2015 |
| CN | 105229451 | 1/2016 |
| CN | 105283756 | 1/2016 |
| EP | 2894464 | 7/2015 |
| JP | S5026593 | 3/1975 |
| JP | S6465443 | 3/1989 |
| JP | H0285753 | 3/1990 |
| JP | H03220448 | 9/1991 |
| JP | H04235338 | 8/1992 |
| JP | H0587760 | 4/1993 |
| JP | H05322828 | 12/1993 |
| JP | H06213851 | 8/1994 |
| JP | H07260728 | 10/1995 |
| JP | 2003262600 | 9/2003 |
| JP | 2006017681 | 1/2006 |
| JP | 2006088088 | 4/2006 |
| JP | 2006133180 | 5/2006 |
| JP | 3173006 | 1/2012 |
| JP | 2013242269 | 12/2013 |
| WO | 03021246 | 3/2003 |
| WO | 2014189119 | 11/2014 |

OTHER PUBLICATIONS

"Office Action of U.K. Counterpart Application", dated Oct. 14, 2021, p. 1-p. 4.

"International Preliminary Report on Patentability of PCT/JP2018/028058; this report contains the following items : PCT/IB/373, PCT/ISA237 (cover sheet), PCT/ISA237 (Box No. I), PCT/ISA237 (Box No. V)", dated Feb. 11, 2020 and Sep. 25, 2018, which is English translation of "Written Opinion of the International Searching Authority", p. 1-p. 16.

M-System Co., Ltd. Development Dept. , "Temperature Sensor: Thermistor", with partial English translation, MS Today, Nov. 2006, p. 14.

Office Action of China Counterpart Application, with English translation thereof, dated Aug. 3, 2022, pp. 1-22.

* cited by examiner

GAS SENSOR, GAS DETECTION DEVICE, GAS DETECTION METHOD, AND DEVICE PROVIDED WITH GAS SENSOR OR GAS DETECTION DEVICE

CROSS-REFERENCE TO RELATED APPLICATION

This application is a 371 application of the international PCT application serial no. PCT/JP2018/028058, filed on Jul. 26, 2018, which claims the priority benefits of Japan application no. 2017-154003, filed on Aug. 9, 2017. The entirety of each of the above-mentioned patent applications is hereby incorporated by reference herein and made a part of this specification.

TECHNICAL FIELD

The present invention relates to a gas sensor which can detect gas molecules, a gas detection device, a gas detection method, a device including the gas sensor and a device including the gas detection device.

DESCRIPTION OF RELATED ART

In the related art, for example, in household electrical appliances, office automation (OA) instruments, food storage devices, medical instruments, and transport devices such as vehicles, in order to detect humidity and specific gases, humidity sensors and gas sensors are used as gas detection devices.

In such gas detection devices, it is necessary to improve the gas detection sensitivity at a low temperature and gas selectivity for selecting a detection target gas.

Meanwhile, humidity sensors including a humidity sensitive resistive element in which a metal resistance wire is surrounded by a type A zeolite, for example, a molecular sieve 5A, are known (refer to Patent Literature 1 and Patent Literature 2).

In addition, in order for a gas sensor to withstand siloxane gases for a long time and to improve gas selectivity, a gas sensor in which a filter made of zeolite, activated alumina, or the like is provided in a housing in which a sensor main body is accommodated has been proposed (refer to Patent Literature 3).

In addition, a humidity sensor using a sensor element including a sensor chip and a humidity sensor using a humidity sensitive thin film formed by polymerizing monomers have been proposed (refer to Patent Literature 4 and Patent Literature 5). In addition, a hydrogen gas sensor in which palladium is used as a hydrogen absorption material, hydrogen is absorbed into solid palladium according to a chemical reaction such as a hydrogenation reaction and thus hydrogen gas is detected has been proposed (refer to Patent Literature 6).

REFERENCE LIST

Patent Literature

Patent Literature 1: Japanese Patent Application Laid-open No. H2-85753
Patent Literature 2: Japanese Patent Application Laid-Open No. H3-220448
Patent Literature 3: Japanese Patent Application Laid-Open No. 2013-242269
Patent Literature 4: Japanese Utility Model (Registered) No. 3173006
Patent Literature 5: Japanese Patent Application Laid-Open No. 2003-262600
Patent Literature 6: WO2014/189119

SUMMARY

Technical Problem

However, the above conventional humidity sensors are based on a principle in which a change in the electrical resistance value according to the water vapor content in the atmosphere is detected and thus the humidity is detected. Thus, in the humidity sensors shown in Patent Literature 1 and Patent Literature 2, a current is caused to flow through a metal resistance wire, adjustment is performed to increase the temperature to a temperature within a range of 300 to 500° C., and thus there are problems of the energy for heating the metal resistance wire becoming large, power consumption becoming large, and the lifespan being shorter.

In addition, in the gas sensor shown in Patent Literature 3, a filter made of zeolite, activated alumina, activated carbon or the like needs to be separately provided, and the humidity sensors shown in Patent Literature 4 and Patent Literature 5 have a problem of the gas detection sensitivity being low at a low temperature. In addition, in Patent Literature 6, since the detection principle is based on a chemical reaction, detection is not possible in the case of an inert gas, for example, helium gas, because no chemical reaction occurs.

The present invention has been made in view of the above problems and an objective of the present invention is to provide a gas sensor, a gas detection device, a gas detection method, and a device including a gas sensor, and a device including a gas detection device through which it is possible to improve gas detection performance and it is possible to reduce variation in output characteristics of individual gas sensors.

Solution to Problem

A gas sensor according to item 1 includes a heat sensitive resistive element having at least a pair of electrodes; a lead part which is connected to the heat sensitive resistive element by welding, while having no inclusions; and a porous gas molecule adsorption material which is thermally coupled to the heat sensitive resistive element and from which specific gas molecules are desorbed by heating.

As the porous gas molecule adsorption material, a zeolite or porous metal complex can be used. As the zeolite, for example, a type A zeolite molecular sieve is suitably used. The porous metal complex is a new material which is a coordination polymer or metal organic framework according to utilization of a metal complex.

In the gas sensor according to item 2, the lead part has a thermal conductivity of 5 W/m·K to 25 W/m·K and a cross-sectional area of 0.001 mm$^2$ to 0.03 mm$^2$, and is formed of a weldable material in the gas sensor according to item 1.

According to the invention, the heat capacity is reduced, and thus a gas sensor having high sensitivity, and excellent thermal response can be realized.

In the gas sensor according to item 3, the heat sensitive resistive element is formed by forming a thin film element layer into a film on a substrate, and the substrate has a thickness of 10 µm to 100 µm in the gas sensor according to item 1 or 2.

According to the invention, the total thickness of the sensor is reduced and the heat capacity is reduced and thus a gas sensor having high sensitivity and excellent thermal response can be realized.

In the gas sensor according to item 4, the porous gas molecule adsorption material is formed into a film on a surface of the heat sensitive resistive element, and the thickness of the formed porous gas molecule adsorption material is 1 µm to 5 µm in the gas sensor according to any one of items 1 to 3.

According to the invention, the heat capacity is reduced, and thus a gas sensor having high sensitivity, and excellent thermal response can be realized.

In the gas sensor according to item 5, the lead part is formed into a foil-like lead frame shape in the gas sensor according to any one of items 1 to 4.

According to the invention, the total thickness of the sensor is reduced and the heat capacity is reduced and thus a gas sensor having high sensitivity and excellent thermal response can be realized.

In the gas sensor according to item 6, the heat sensitive resistive element is a thermistor in the gas sensor according to any one of items 1 to 5.

When the thermistor is used, a thermal runaway phenomenon unique to the thermistor can be utilized and the sensitivity of the gas sensor can be increased.

The gas sensor according to item 7 includes a heating and/or cooling element which maintains the gas sensor at a constant temperature in a gas sensor according to any one of items 1 to 6.

The heating and/or cooling element includes an element having a function of either heating or cooling or an element having a function of both heating and cooling. For example, a thermoelectric element such as a heater and a Peltier element can be applied.

When the gas sensor remains at a constant temperature, various disturbance factors related to the temperature can be reduced and the sensitivity of the gas sensor can be increased.

In the gas sensor according to item 8, the heating and/or cooling element is a thermoelectric element in the gas sensor according to item 7.

A gas detection device according to item 9 includes the gas sensor according to any one of items 1 to 6, and a heating and/or cooling device which maintains the gas sensor at a constant temperature.

As the heating and/or cooling device, for example, a temperature adjusting device including a thermoelectric element can be applied. However, the heating and/or cooling device is not limited to a specific device.

According to the invention, when the gas sensor remains at a constant temperature, various disturbance factors related to the temperature can be reduced and the sensitivity of the gas sensor can be increased.

A gas detection method according to item 10 is a gas detection method for a gas sensor including a heat sensitive resistive element having at least a pair of electrodes, a lead part which is connected to the heat sensitive resistive element by welding, while having no inclusions, and a porous gas molecule adsorption material which is thermally coupled to the heat sensitive resistive element and from which specific gas molecules are desorbed by heating. The method includes a step of maintaining the gas sensor at a constant temperature; a heating step of heating the porous gas molecule adsorption material; and a detecting step of detecting a specific gas according to change in an output of the heat sensitive resistive element due to the heating.

In the gas detection method according to item 11, in order to detect the specific gas, an output of a reference gas is measured in advance in the gas detection method according to item 10.

In the gas detection method according to item 12, in the detecting step, a concentration of the specific gas is detected by comparing a measurement result of the output of the reference gas with a measurement result of an output of the specific gas in advance in the gas detection method according to item 11.

In the gas detection method according to item 13, in the heating step, an overpower is supplied to the heat sensitive resistive element to put the heat sensitive resistive element into a thermal runaway state in the gas detection method according to any one of items 10 to 12.

In the gas detection method according to item 14, the constant temperature is 10° C. or lower in the gas detection method according to item 13.

When the temperature of the gas sensor is lowered, the sensor becomes sensitive and can detect a trace amount of gas.

A device including the gas sensor according to item 15, includes the gas sensor according to any one of items 1 to 8.

The device including the gas sensor can be provided in and applied to various devices such as medical instruments, vehicles, household electrical appliances, OA instruments, and food storage devices in order to detect gas molecules and humidity. Applicable devices are not particularly limited.

A device including the gas detection device according to item 16 includes the gas detection device according to item 9.

The device including the gas detection device can be provided in and applied to various devices such as medical instruments, vehicles, household electrical appliances, OA instruments, and food storage devices in order to detect gas molecules and humidity. Applicable devices are not particularly limited.

Advantageous Effects of Invention

According to the present invention, it is possible to provide a gas sensor, a gas detection device, a gas detection method, and a device including a gas sensor, and a device including a gas detection device through which it is possible to improve gas detection performance and it is possible to reduce variation in output characteristics of individual gas sensors.

DESCRIPTION OF THE EMBODIMENTS

Figure 1:
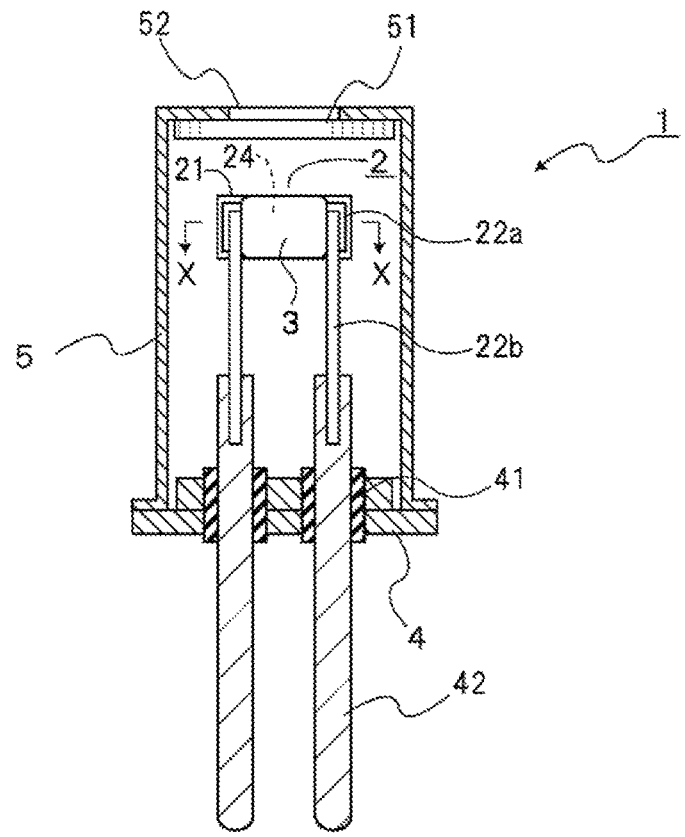
FIG. 1 is a cross-sectional view showing a gas sensor according to a first embodiment of the present invention.
Figure 2:
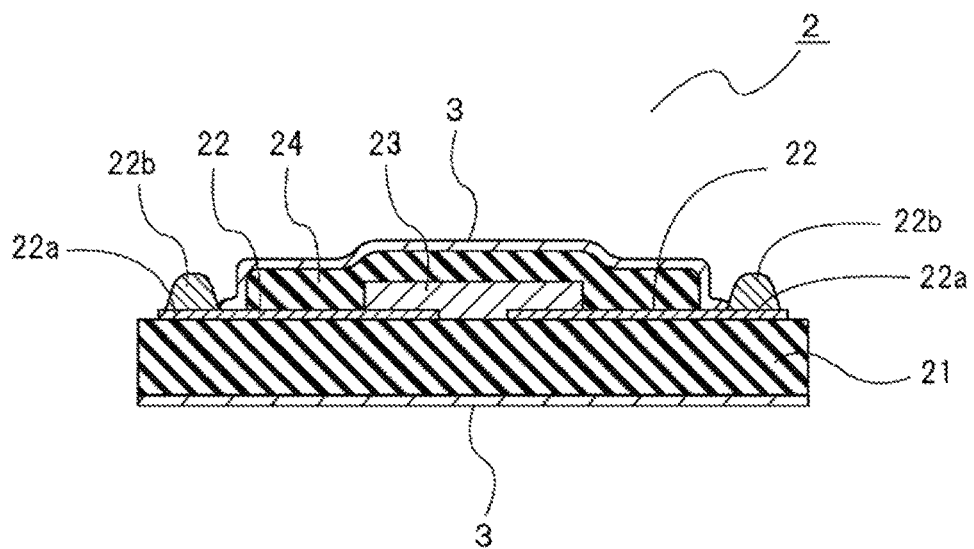
FIG. 2 is a cross-sectional view taken along the line X-X in FIG. 1.
Figure 3:
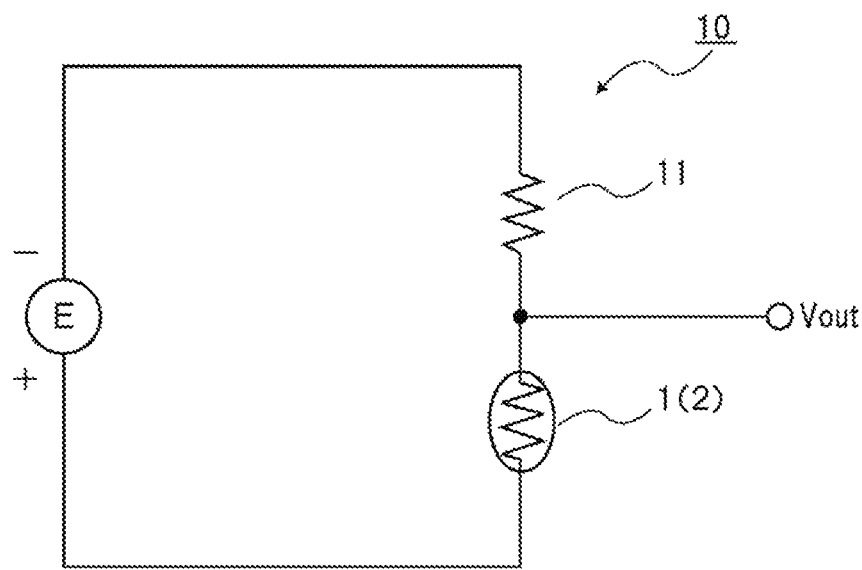
FIG. 3 is a connection diagram for detecting characteristics of this gas detection device.
Figure 4:
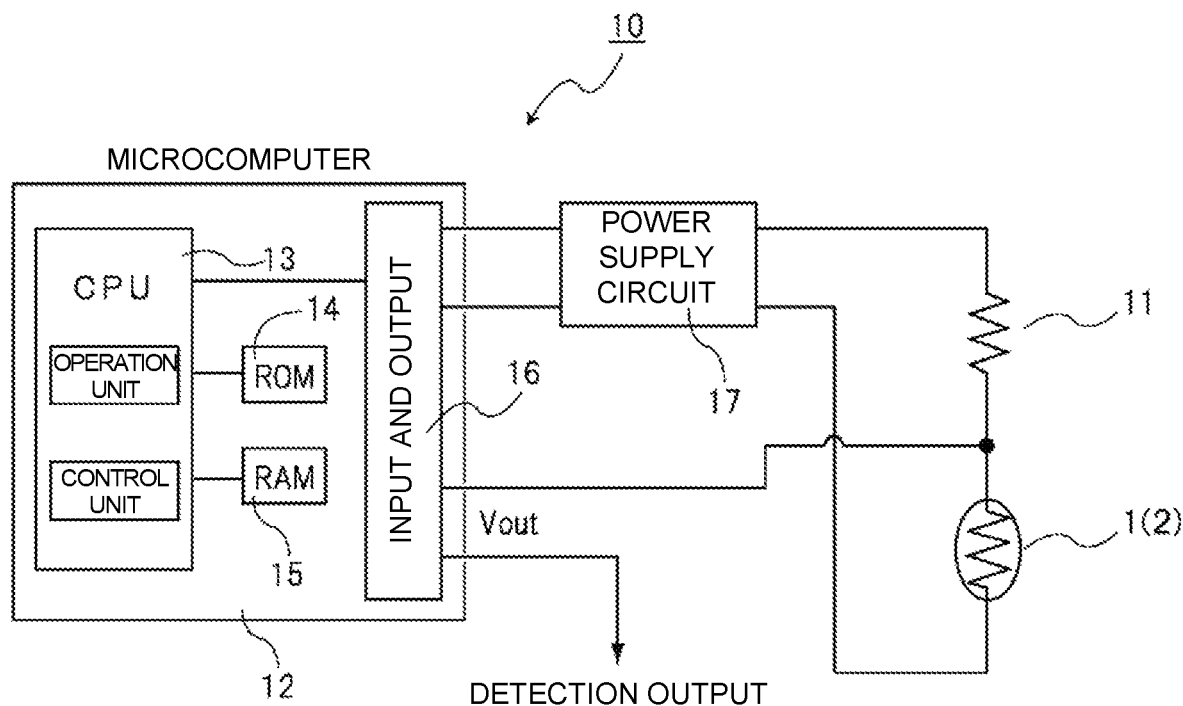
FIG. 4 is a block configuration diagram showing this gas detection device.
Figure 5:
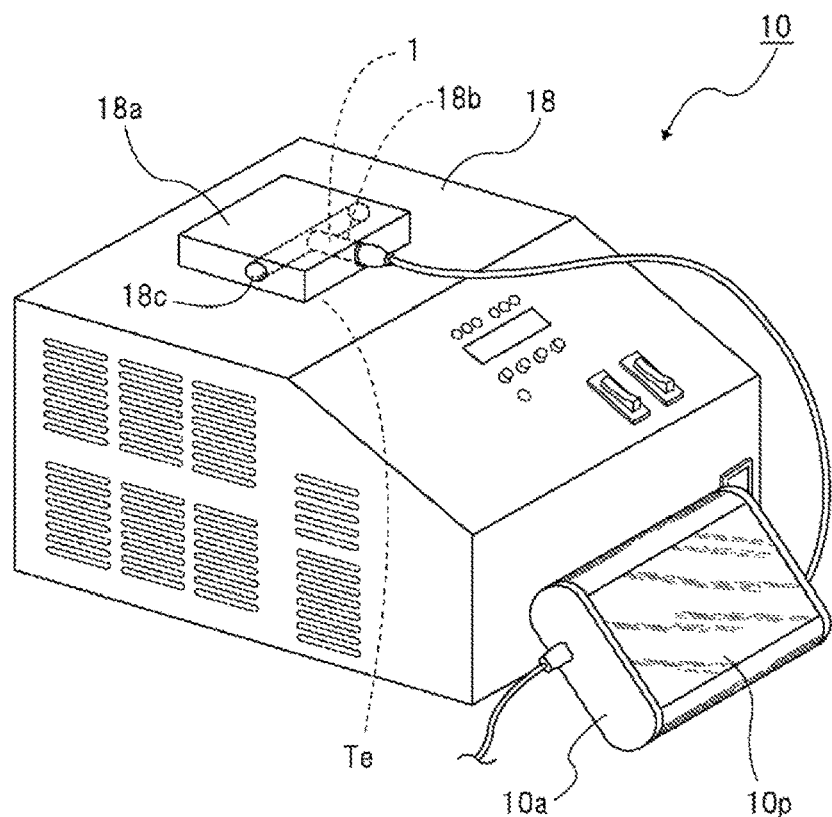
FIG. 5 is a diagram of a configuration example schematically showing a measurement method for this gas detection device.

A gas sensor, a gas detection device and a gas detection method according to a first embodiment of the present invention will be described below with reference to FIG. 1 to FIG. 10. FIG. 1 and FIG. 2 are cross-sectional views showing a gas sensor. FIG. 3 is a connection diagram for detecting characteristics of the gas detection device. FIG. 4 is a block configuration diagram showing the gas detection device. FIG. 5 is a configuration example schematically showing a measurement method for the gas detection device. In addition, FIG. 6 to FIG. 10 are graphs for explaining output characteristics of the gas sensor.

A shown in FIG. 1 and FIG. 2, a gas sensor 1 includes a heat sensitive resistive element 2, a gas molecule adsorption material 3, a base member 4 and an exterior case 5. The gas sensor 1 is a sensor that detects water vapor gas (water molecules), hydrogen gas and the like in the atmosphere. Here, in the drawings, scales of members are appropriately changed in order for the members to be set to recognizable sizes.

The heat sensitive resistive element 2 is a thin film thermistor, and is a detection heat sensitive resistive element. The heat sensitive resistive element 2 includes a substrate 21, and a conductive layer 22, a thin film element layer 23 and a protective insulating layer 24 formed on the substrate 21.

The substrate 21 has a substantially rectangular shape and is formed using a ceramic material such as insulating alumina, aluminum nitride, and zirconia or a semiconductor silicon, germanium, or the like. An insulating thin film is formed on one surface of the substrate 21 according to a sputtering method. Specifically, the substrate 21 may be made of an alumina material and is extremely thin and formed to have a thickness of 10 μm to 100 μm. When such an extremely thin substrate 21 is used for the heat sensitive resistive element 2, the gas sensor 1 having a reduced heat capacity, high sensitivity, and excellent thermal response can be realized.

The conductive layer 22 forms a wiring pattern and is formed on the substrate 21. The conductive layer 22 is formed by forming a metal thin film according to a sputtering method. Regarding metal materials thereof, precious metals such as platinum (Pt), gold (Au), silver (Ag), and palladium (Pd), and alloys thereof, for example, an Ag—Pd alloy, are applied. In addition, at both ends of the substrate 21, an electrode part 22a electrically connected to the conductive layer 22 is formed integrally with the conductive layer 22.

The thin film element layer 23 is a thermistor composition, and is composed of an oxide semiconductor having a negative temperature coefficient. The thin film element layer 23 is formed into a film on the conductive layer 22 according to a sputtering method or the like and is electrically connected to the conductive layer 22.

For example, the thin film element layer 23 is composed of two or more elements selected from among transition metal elements such as manganese (Mn), nickel (Ni), cobalt (Co), and iron (Fe). The protective insulating layer 24 is formed to cover the thin film element layer 23 and the conductive layer 22. The protective insulating layer 24 is a protective glass layer formed of borosilicate glass.

In addition, a metal lead part 22b is bonded to the electrode part 22a by welding and electrically connected thereto. Specifically, the lead part 22b is formed of, for example, a material having low thermal conductivity such as Constantin or Hastelloy (registered trademark) and its thermal conductivity is preferably 5 W/m·K to 25 W/m·K. These are connected in a state in which they have been welded by laser welding. Therefore, respective metals of the electrode part 22a and the lead part 22b are melted and bonded. Therefore, since there are no additional materials such as a filler material (brazing filler material) used in the case of soldering or the like between the electrode part 22a and the lead part 22b, that is, since there are no inclusions, a heat capacity can be reduced, the thermal time constant can be reduced and thus the thermal responsiveness of the heat sensitive resistive element 2 can be increased. Here, for the lead part 22b, a linear component having a circular cross-section or a narrow plate component having a frame shape can be used. The form of the lead part 22b is not particularly limited. When the lead part 22b is a linear component, it has a narrow plate-like foil shape with a diameter of φ30 μm to φ100 μm, and in the case of the lead frame shape, preferably, the width is 80 to 200 μm, and the thickness is 10 μm to 60 μm. In addition, the cross-sectional area of the lead part 22b is desirably 0.001 mm$^2$ to 0.03 mm$^2$.

In this manner, the material of the lead part 22b has a thermal conductivity of 5 W/m·K to 25 W/m·K, and a material that can be welded is selected and the cross-sectional area of the lead part 22b is set to 0.001 mm$^2$ to 0.03 mm$^2$. Therefore, the heat capacity and heat dissipation amount of the heat sensitive resistive element 2 are reduced and the gas sensor 1 having high sensitivity and excellent thermal responsiveness can be realized. In particular, when a foil is used for the lead part, these effects are further improved.

In addition, the heat sensitive resistive element is not limited to a thin film thermistor, and may be composed of a thin film platinum resistive element. In addition, a thermistor element composed of a metal wire such as a platinum wire and a wire of its alloys or a semiconductor such as a metal oxide, silicide, or nitride may be used. The heat sensitive resistive element may be composed of a thermocouple element such as a thermocouple or a thermopile in which a plurality of thermocouples are connected in series and is not particularly limited.

The gas molecule adsorption material 3 is provided by being thermally coupled to the heat sensitive resistive element 2 configured as described above. Specifically, the gas molecule adsorption material 3 is formed into a film on the surface of the heat sensitive resistive element 2. More specifically, the gas molecule adsorption material 3 is maintained in a state of being formed into a film on the surface of the protective insulating layer 24 and the surface on the other surface side (rear surface side) of the substrate 21.

Therefore, the heat sensitive resistive element 2 and the gas molecule adsorption material 3 are thermally coupled to the thin film element layer 23 via the protective insulating layer 24 and the substrate 21. That is, heat is mutually conducted between the heat sensitive resistive element 2 and the gas molecule adsorption material 3.

The gas molecule adsorption material 3 is a porous adsorption material, and is formed by, for example, forming a type A zeolite molecular sieve 3A (with a pore diameter of 0.3 nm) into a film on the surface of the heat sensitive resistive element 2. For this formation, water and sodium silicate are added as a Si source and water, aluminum hydroxide, and sodium hydroxide are added as an Al source to prepare respective solutions, and these solutions are mixed and stirred to form a gel. Then, a support that has been treated in advance (heat sensitive resistive element) and the gel are put into an oil bath and hydrothermally reacted at 100° C. for 4 hours to produce a film.

The thickness of the gas molecule adsorption material 3 is 1 μm to 5 μm. When such an extremely thin functional film can be formed on the heat sensitive resistive element 2, the gas sensor 1 having a small heat capacity, high sensitivity and excellent thermal responsiveness can be realized. Here, a film forming method for the gas molecule adsorption material 3 is not particularly limited to a specific method.

In addition, regarding the gas molecule adsorption material 3, according to a detection target gas, molecular sieves 4A, 5A, 13X, a high silica type zeolite, a silver zeolite substituted with metal ions or the like, and a porous metal complex can be used.

The base member 4 is a metal member formed in a substantially disk shape, and a conductive terminal part 42 is inserted thereinto via an insulating member 41. The lead part 22b led from the heat sensitive resistive element 2 is electrically connected to the conductive terminal part 42 by welding, soldering, or the like. The insulating member 41 is formed of an insulating material such as glass or a resin.

Here, when the base member 4 is formed of an insulating material, the insulating member 41 can be omitted. In addition, the conductive terminal part 42 may be composed of a printed wiring board or the like.

The exterior case 5 is a metal member which is formed in a substantially cylindrical shape and has favorable thermal conductivity, and has one end side that is open and the other end side on which a circular opening 52 in which a ventilation part 51 is provided is formed. The exterior case 5 has one end side that is attached to the base member 4 and has a function of covering and protecting the heat sensitive resistive element 2.

The ventilation part 51 is formed of a member which reduces an influence of outside air and has an air permeability that allows gases to flow in and out, and is desirably composed of a material such as a wire mesh, a non-woven fabric or a porous sponge. The ventilation part 51 is provided by press-fitting or bonding to the inner peripheral side of the exterior case 5. In addition, the present invention is not limited to the ventilation part 51 that is provided in the exterior case 5. The ventilation part 51 may be provided in the base member 4 or may be provided in a part that is formed in a gap between the exterior case 5 and the base member 4.

Here, the exterior case 5 can be formed of a ceramic or resin material. In this case, a metal plating or the like may be applied so that the inner wall surface of the exterior case 5 has a function of reflecting infrared rays.

As shown in FIG. 3, in a gas detection device 10, a power supply (voltage source) E is connected to the gas sensor 1. Specifically, a resistor 11 and the gas sensor 1 (the heat sensitive resistive element 2) are connected to the power supply E in series, an output terminal is connected between the resistor 11 and the heat sensitive resistive element 2, and an output voltage Vout is detected using a voltage between both ends of the heat sensitive resistive element 2 as a voltage applied to the sensor. The resistor 11 is a resistor for protecting from an overcurrent.

In the gas sensor 1 of the present embodiment described above, the metal lead part 22b is bonded to the electrode part 22a in the heat sensitive resistive element 2 by welding. Here, a gas sensor in which a metal lead part was bonded by soldering to an electrode part was used as a comparative example, and output characteristics of both the gas sensor 1 of the present embodiment and the gas sensor of the comparative example were compared and measured.

As a result, it was found that the gas sensor of the comparative example had a greater variation in output characteristics of individual gas sensors than the gas sensor 1 of the present embodiment. This is thought to be caused by the fact that, in the gas sensor of the comparative example, there is an inclusion of a filler material (brazing filler material) between the electrode part and the lead part, variation in the amount of the inclusion tends to occur, and this causes the variation in output characteristics.

Therefore, in the gas sensor 1 of the present embodiment, since there are no inclusions as in the gas sensor of the comparative example, it is possible to reduce the variation in output characteristics of individual gas sensors 1 and improve the reliability.

Next, as shown in FIG. 4, in the present embodiment, in the gas detection device 10, a microcomputer (hereinafter referred to as a "microcom") 12 as a control means performs overall control. The microcomputer 12 chiefly includes a central processing unit (CPU) 13 having an operation unit and a control unit, a read only memory (ROM) 14 and a random access memory (RAM) 15 as a storage means, and an input and output control means 16. Further, a power supply circuit 17 is connected to the input and output control means 16. In addition, the circuit shown in FIG. 3 is connected to the power supply circuit 17.

The power supply circuit 17 includes the power supply E and has a function of applying a voltage of the power supply E to the heat sensitive resistive element 2 and controlling supply of electric power to the heat sensitive resistive element 2. Specifically, according to a program stored in the storage means of the microcomputer 12, electric power supplied from the power supply E in the power supply circuit 17 is controlled. In addition, the output voltage Vout is input to the microcomputer 12 and subjected to arithmetic processing and output as a detection output.

Here, in the present embodiment, supply of electric power from the power supply E is performed by, for example, a means composed of the microcomputer 12 and the power supply circuit 17, that is, an electric power supply unit. The electric power supply unit only needs to have a function of supplying electric power to the gas sensor 1, specifically, a function of supplying electric power from the power supply E to the heat sensitive resistive element 2, and is not limited to a particularly specific member or part.

Next, FIG. 5 shows a configuration example of the gas detection device 10 including a thermoelectric element Te as a temperature adjusting element which maintains the gas sensor 1 at a constant temperature. In this configuration example, a temperature control unit 18 including the thermoelectric element Te therein is shown as a heating and/or cooling device which maintains the gas sensor 1 at a constant temperature. Specifically, the gas detection device 10 includes a detection circuit part 10a in which the microcomputer 12 and the power supply circuit 17 shown in FIG. 4 are accommodated and the temperature control unit 18.

The detection circuit part 10a has a circuit component housed in a housing, a display panel 10p is provided on the front side, and the gas sensor 1 which is connected by an electrical wire.

The temperature control unit 18 is a temperature adjusting device which can control cooling and heating, and includes a Peltier element therein as the thermoelectric element Te, and can set the temperature in a range of −20° C. to +80° C.

In addition, an installation member 18a of the gas sensor 1 formed of a material having favorable heat conduction such as copper is disposed on a plate (not shown) on the upper surface of the temperature control unit 18. An insertion hole 18b and a flow hole 18c through which a gas in the atmosphere can flow to the gas sensor 1 are formed in the installation member 18a.

The gas sensor 1 is inserted into the insertion hole 18b, and in the inserted state, gas can flow into and out from the ventilation part 51 of the gas sensor 1 through the flow hole 18c so that a gas can be detected.

Here, the gas detection device 10 includes a heating and/or cooling device which maintains the gas sensor 1 at a constant temperature, specifically, the thermoelectric element Te. A Peltier element can be applied as the thermoelectric element and a heater or the like can be applied as the heating element. In addition, it is desirable that the constant temperature have an accuracy of ±0.1° C.

When the temperature of the gas sensor 1 is lowered, the sensor becomes more sensitive, and can detect, for example, a trace amount such as 1 ppm or less of a gas. On the other hand, when the temperature of the gas sensor 1 increases, the sensor becomes less sensitive, and can easily detect a gas with a high concentration.

Next, the operation of the gas detection device 10 will be described with reference to FIG. 3, FIG. 4 and FIG. 5 to FIG. 10 together. In the present embodiment, a case in which a detection target gas is hydrogen ($H_2$) will be shown. For example, a gas detection device applied to a hydrogen station or a fuel cell vehicle under an environment in which a predetermined amount of hydrogen ($H_2$) may exist may be used.

First, the porous gas molecule adsorption material 3 will be described. The gas molecule adsorption material 3 is the type A zeolite molecular sieve 3A (with a pore diameter of 0.3 nm). The gas molecule adsorption material 3 exhibits a molecular sieve effect and adsorbs only molecules with a diameter smaller than a pore diameter. Therefore, the material adsorbs hydrogen ($H_2$), helium (He), water vapor (water molecule) ($H_2O$) and ammonia ($NH_3$) in the atmosphere but does not adsorb nitrogen ($N_2$) and oxygen ($O_2$). Therefore, it is possible to selectively detect a gas according to the size of molecules and it is possible to improve the selectivity of a detection target gas.

In addition, the gas molecule adsorption material 3 generally adsorbs and desorbs molecules and thus the temperature changes. Therefore, when the gas molecule is hydrogen ($H_2$), a phenomenon in which the gas molecule adsorption material 3 is heated to desorb hydrogen ($H_2$), and thus the temperature changes occurs.

FIG. 6 to FIG. 10 show graphs showing measurement results for explaining output characteristics of the gas sensor. This gas detection is for detecting a concentration of a trace amount of hydrogen ($H_2$) and uses a thermal runaway phenomenon of the heat sensitive resistive element 2.

As shown in the drawings, an ambient temperature (temperature of the gas sensor 1) is kept constant at 5° C. by the thermoelectric element Te, the voltage of the power supply E is kept constant at 3.45 V, nitrogen ($N_2$) is set to 100%, a voltage (V) applied to the sensor in an atmosphere containing 1 ppm or 2 ppm of hydrogen ($H_2$) based on nitrogen ($N_2$), the sensor temperature (° C.) and the sensor output (mV) are measured. The horizontal axis represents time (seconds) and the vertical axis represents voltage (mV) of a sensor output. Here, the sensor output indicates a voltage difference compared with respect to a voltage applied to the sensor when nitrogen ($N_2$) is set to 100%. Therefore, in order to detect a specific gas (hydrogen), an output of a reference gas (100% nitrogen) is measured in advance.

As shown in FIG. 4, when the ambient temperature (the temperature of the gas sensor 1) is kept constant at 5° C., the gas detection device 10 is driven, and according to an output signal from the microcomputer 12, the power supply E of the power supply circuit 17 is applied to the heat sensitive resistive element 2 as a constant voltage of 3.45 V. This state is a state in which electric power is supplied so that the heat sensitive resistive element 2 is heated. Here, it is known that, when an overpower is supplied to the heat sensitive resistive element 2 made of a thermistor composition, a thermal runaway phenomenon occurs.

Figure 6:
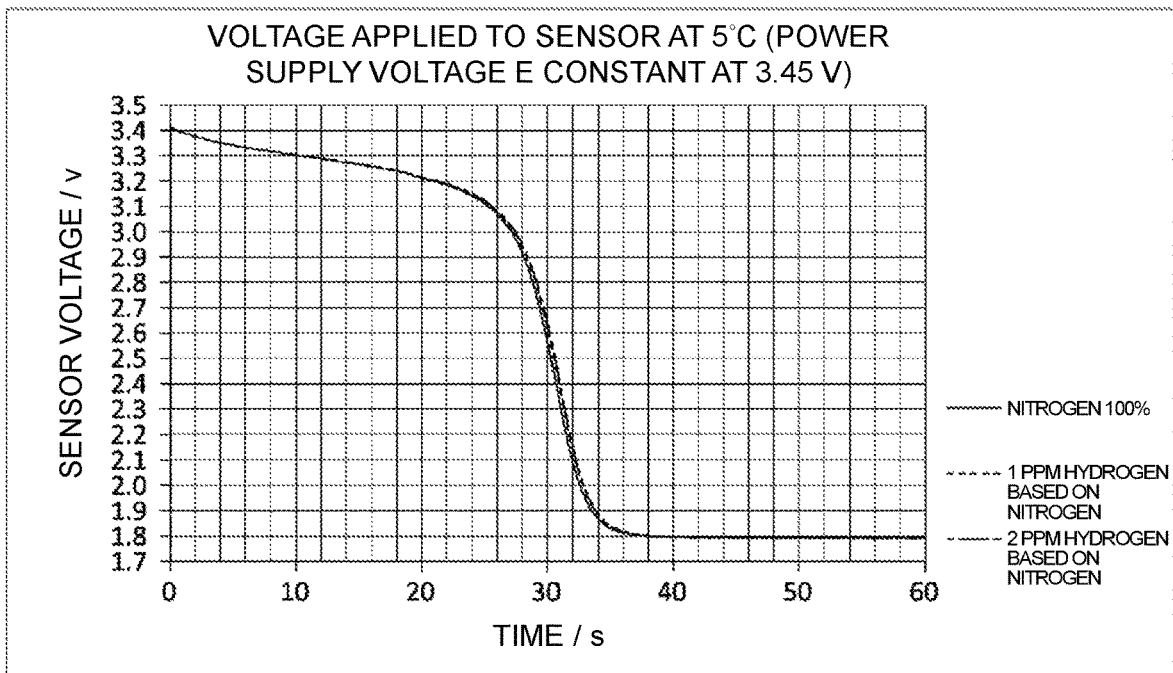
FIG. 6 is a graph for explaining output characteristics of a gas sensor and is a graph showing a voltage applied to a sensor with respect to a hydrogen concentration at 5° C.
Figure 7:
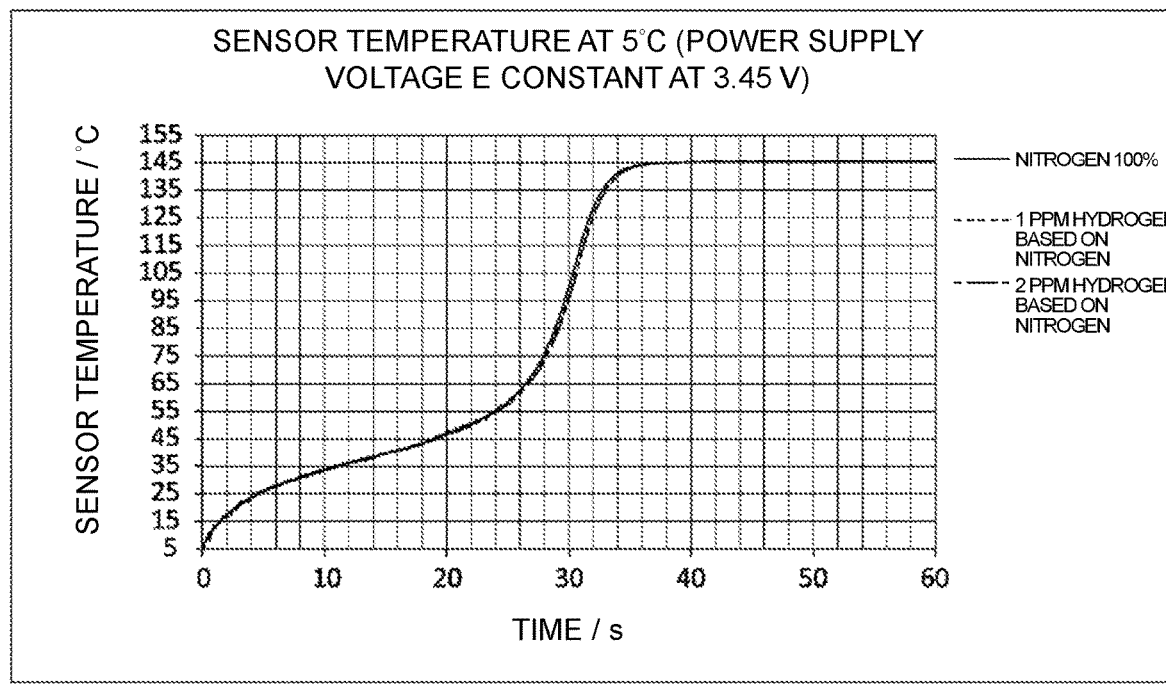
FIG. 7 is a graph showing a sensor temperature with respect to a hydrogen concentration at 5° C.

As shown in FIG. 6 and FIG. 7, when a voltage of 3.45 V is applied to the heat sensitive resistive element 2 and electric power is supplied, a voltage applied to the sensor sharply drops in about 30 seconds (refer to FIG. 6), and the temperature of the sensor sharply increases (refer to FIG. 7), and there is a tendency for the value to become almost constant thereafter. Such a sharp change indicates that an overpower is supplied to the heat sensitive resistive element 2 and the heat sensitive resistive element 2 is in a thermal runaway state.

Figure 9:
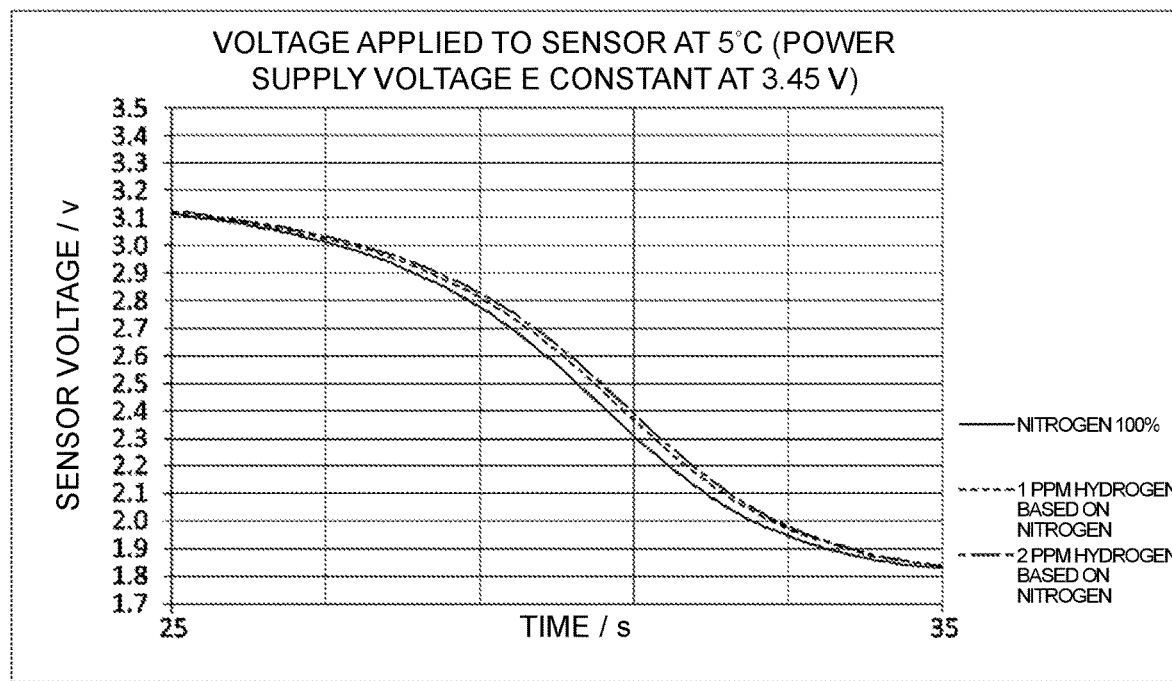
FIG. 9 is a diagram corresponding to FIG. 6 and is a graph with the range of the time axis changed.
Figure 10:
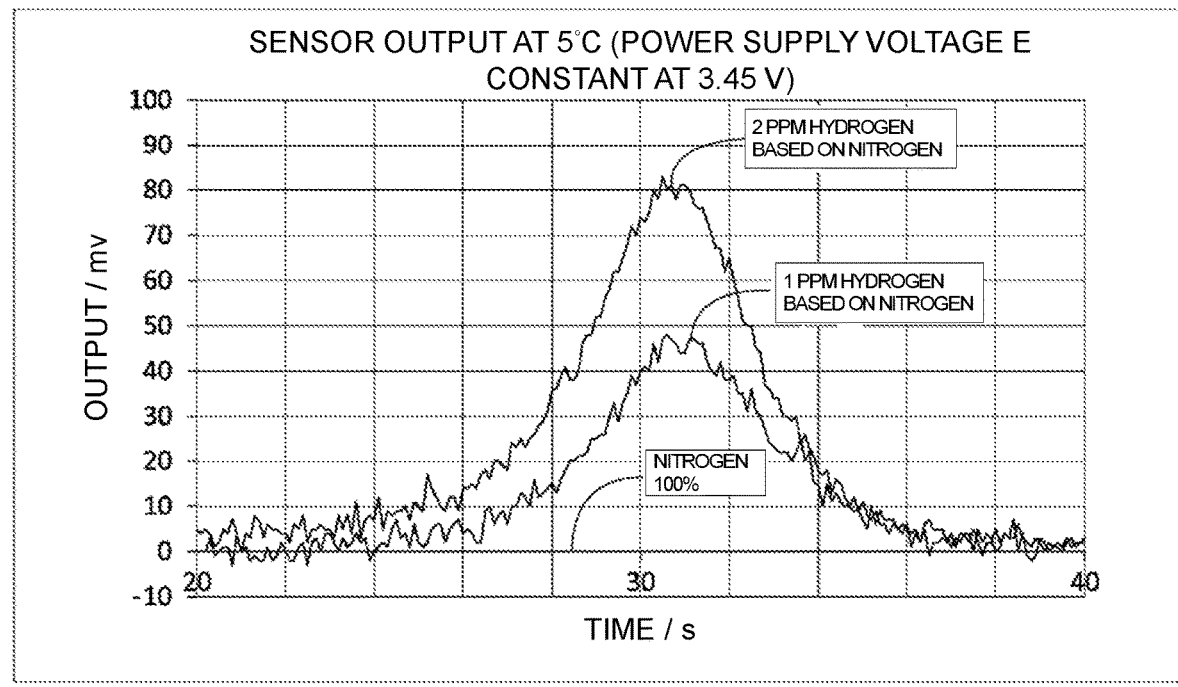
FIG. 10 is a diagram corresponding to FIG. 8 and is a graph with the range of the time axis changed.

Here, as shown in FIG. 6 and FIG. 7, there is almost no difference in the change between nitrogen ($N_2$) 100%, hydrogen ($H_2$) 1 ppm, and hydrogen ($H_2$) 2 ppm, and this is because the amount of hydrogen ($H_2$) is extremely small amount and it is difficult to show the relationship with the scale of the graph. Therefore, FIG. 9 shows a voltage applied to the sensor in a range corresponding to 25 seconds to 35 seconds on the time axis in FIG. 6. In addition, FIG. 10 shows a sensor output in a range corresponding to 20 seconds to 40 seconds on the time axis in FIG. 8 for the sake of prudence.

When a voltage of 3.45 V is applied to the heat sensitive resistive element 2 and electric power is supplied, a current is caused to flow through the heat sensitive resistive element 2, electric power is supplied, the heat sensitive resistive element 2 is self-heated, and the gas molecule adsorption material 3 thermally coupled to the heat sensitive resistive element 2 is heated. When the gas molecule adsorption material 3 is heated, hydrogen ($H_2$) adsorbed on the gas molecule adsorption material 3 is desorbed and the temperature of the gas molecule adsorption material 3 changes according to the concentration. Therefore, the temperature of the heat sensitive resistive element 2 (the temperature of the sensor) changes according to the concentration of hydrogen ($H_2$), and a voltage applied to the sensor changes according to the concentration of hydrogen ($H_2$) (refer to FIG. 9). In this manner, since the sensor temperature, a voltage applied to the sensor, and the sensor output change according to the concentration of hydrogen ($H_2$), it is possible to detect the concentration of hydrogen ($H_2$).

Figure 8:
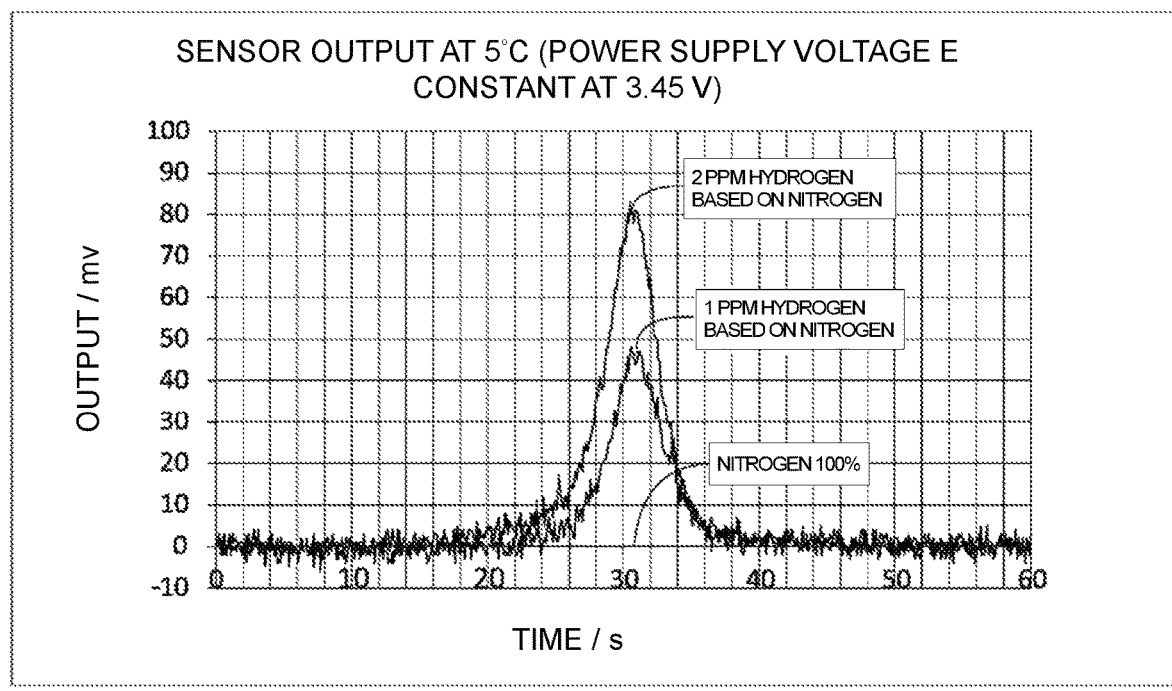
FIG. 8 is a graph showing a sensor output with respect to a hydrogen concentration at 5° C.

Specifically, when electric power is supplied to the heat sensitive resistive element 2, hydrogen ($H_2$) adsorbed on the gas molecule adsorption material 3 is desorbed, the temperature of the gas molecule adsorption material 3 changes, and the output corresponding to the concentration of hydrogen ($H_2$) is calculated by the microcomputer 12 and can be obtained as a pattern of the sensor output (refer to FIG. 8). Since the pattern of the change in the sensor output according to the concentration of hydrogen ($H_2$) is stored in advance in the storage means of the microcomputer 12, the microcomputer 12 performs a calculation operation of comparing the obtained pattern of the sensor output with the pattern stored in advance and calculates and outputs the concentration of hydrogen ($H_2$) as a detection output. Thus, it is possible to detect the concentration of hydrogen ($H_2$).

When the thermal runaway phenomenon of the heat sensitive resistive element 2 as described above is used, even in the concentration of a trace amount of hydrogen ($H_2$), it is possible to largely change the sensor output and it is possible to detect the concentration of a trace amount of hydrogen ($H_2$).

This gas detection method includes a step of maintaining the gas sensor 1 at a constant temperature, a heating step of heating the porous gas molecule adsorption material 3, and a detecting step of detecting a specific gas according to the change in the output of the heat sensitive resistive element 2 due to heating. In addition, in order to detect a specific gas, the output of a reference gas is measured in advance. In addition, in the detecting step, the concentration of the specific gas is detected by comparing the measurement result of the output of the reference gas with the measurement result of the output of the specific gas in advance. Furthermore, in this gas detection method, in the heating step, supply of an overpower to the heat sensitive resistive element 2 to put the heat sensitive resistive element 2 into a thermal runaway state is included, and an overpower is supplied to the heat sensitive resistive element 2 to put the heat sensitive resistive element 2 into a thermal runaway state.

Here, based on the results of measurement under various conditions, it is confirmed that the thermal runaway phenomenon of the heat sensitive resistive element 2 tends to occur when the ambient temperature (the temperature of the gas sensor 1) is a low temperature (10° C. or lower) and tends to occur when the heat capacity of the heat sensitive resistive element 2 is small.

According to the present embodiment described above, since the lead part 22b is connected to the heat sensitive resistive element 2 by welding, the heat capacity can be reduced, the thermal responsiveness can be increased, the variation in output characteristics of individual gas sensors 1 can be reduced, and the reliability can be improved.

In addition, since the gas molecule adsorption material 3 is formed into a film on the surface of the heat sensitive resistive element 2, the heat capacity can be reduced. In addition, since the thickness of the substrate 21 is set to 10 µm to 100 µm and the diameter and thickness of the lead part 22b are small, it is possible to contribute to reducing the heat capacity and promote the high-speed response.

In addition, when the thermal runaway phenomenon of the heat sensitive resistive element 2 is used, it is possible to detect the concentration of a trace amount of hydrogen ($H_2$) gas.

Figure 11:
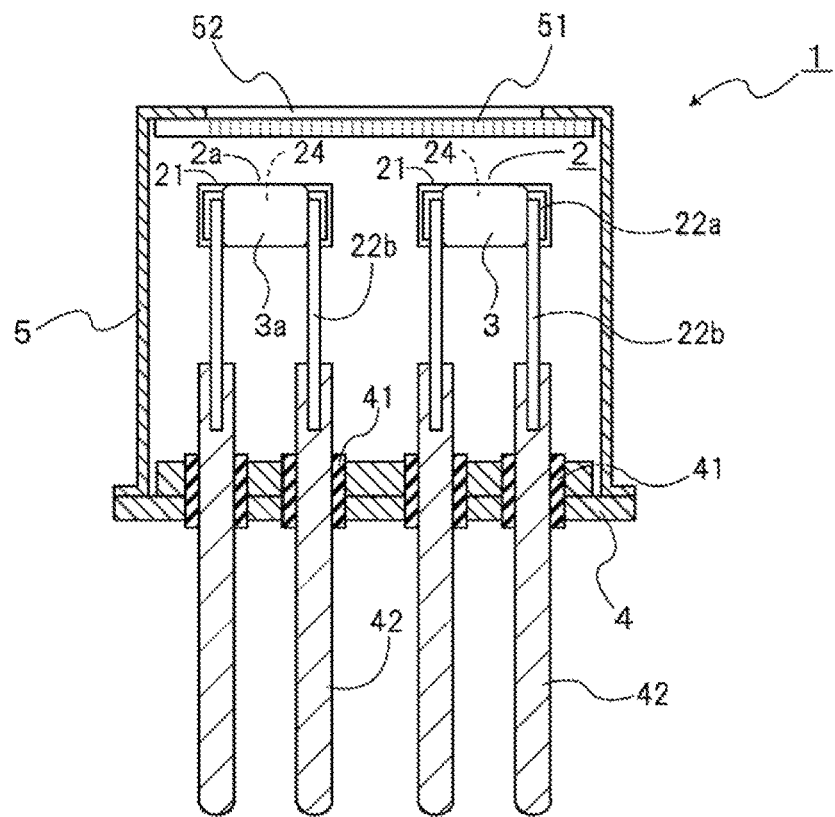
FIG. 11 is a cross-sectional view showing a gas sensor according to a second embodiment of the present invention.

Next, a second embodiment of the present invention will be described with reference to FIG. 11. FIG. 11 is a cross-sectional view showing a gas sensor. Here, parts that are the same as or correspond to those in the first embodiment will be denoted with the same reference numerals and redundant descriptions will be omitted.

As shown in FIG. 11, the gas sensor 1 of the present embodiment is a sensor that detects a concentration of a gas in the atmosphere and includes a pair of heat sensitive resistive elements. That is, the detection heat sensitive resistive element 2 and a compensation heat sensitive resistive element 2a are provided so that they are covered with the exterior case 5. The gas molecule adsorption materials 3 and 3a are formed into a film on the surfaces of the detection heat sensitive resistive element 2 and the compensation heat sensitive resistive element 2a. The detection heat sensitive resistive element 2 and the compensation heat sensitive resistive element 2a have basically the same configuration, but they have a different configuration of the gas molecule adsorption material 3a provided in the compensation heat sensitive resistive element 2a. The gas molecule adsorption material 3a is a material having different adsorption properties from the porous gas molecule adsorption material 3, and an inactivated type A zeolite molecular sieve 3A is used.

Although the inactivated molecular sieve 3A hardly adsorbs gas molecules, it has the same physical properties as the molecular sieve 3A provided in the detection heat sensitive resistive element 2, has the same thermal properties, and has substantially the same heat capacity.

Figure 12:
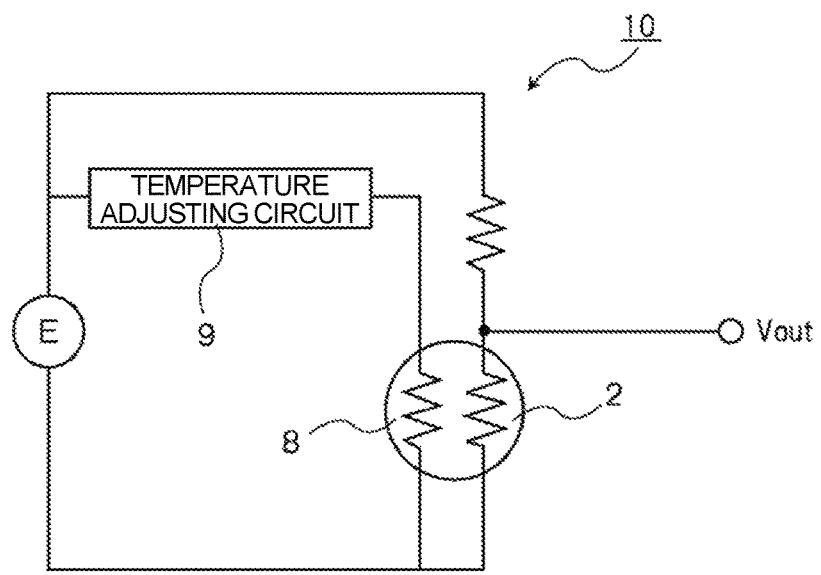
FIG. 12 is a connection diagram for detecting characteristics a gas detection device according to a third embodiment of the present invention.
Figure 13:
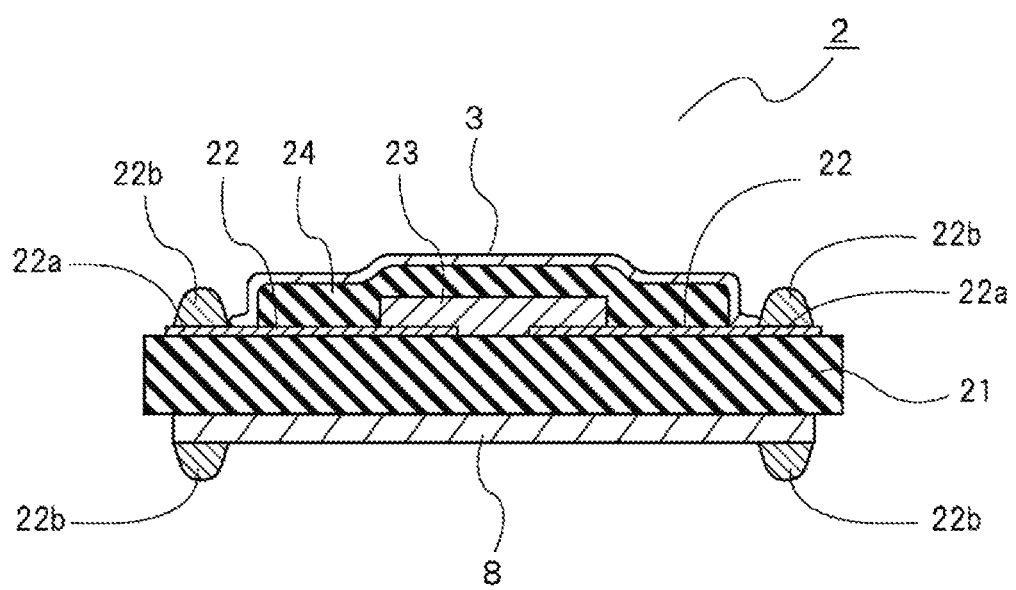
FIG. 13 is a cross-sectional view corresponding to FIG. 2 showing this heat sensitive resistive element.

Next, a third embodiment of the present invention will be described with reference to FIG. 12 and FIG. 13. FIG. 12 is a connection diagram for detecting characteristics of a gas detection device. FIG. 13 is a cross-sectional view showing a heat sensitive resistive element. Here, parts that are the same as or correspond to those in the first embodiment will be denoted with the same reference numerals and redundant descriptions will be omitted.

As shown in FIG. 12, the gas sensor 1, that is, a heating or cooling element 8 as a temperature adjusting element which heats or cools the heat sensitive resistive element 2 and the gas molecule adsorption material 3 and maintains it at a constant temperature, is connected to the gas detection device 10. The temperature of the heating or cooling element 8 is controlled by a temperature adjusting circuit 9 and thus the heat and cooling pattern can be arbitrarily set. Regarding a typical heating or cooling element, a resistor or a thermoelectric element is used.

As described above, when the heat sensitive resistive element 2 is self-heated to perform heat control, since a resistance value of the heat sensitive resistive element 2 changes according to the temperature, the control may be difficult. In such a case, heating and cooling control can function effectively.

FIG. 13 is a cross-sectional view corresponding to FIG. 2 in the first embodiment. Since the gas molecule adsorption material 3 is formed into a film on the protective insulating layer 24, the heating or cooling element 8 is provided on the rear surface side of the substrate 21. Here, a thermistor may be used as the heating or cooling element 8.

In addition, of course, regarding the heating or cooling element 8, not only an element having a function of either heating or cooling but also an element having a function of both heating and cooling can be applied. Therefore, specifically, a heating and/or cooling element can be used.

In the gas sensors and gas detection devices of the above embodiments, the detection target gas is not limited, and hydrogen ($H_2$), water vapor (water molecule) ($H_2O$), helium (He), ammonia (NH$_3$), and the like can be detected, and the gas sensors and gas detection devices can be provided in and applied to various devices such as medical instruments, vehicles, household electrical appliances, OA instruments, and food storage devices. Applicable devices are not particularly limited.

Here, the present invention is not limited to the configuration of the above embodiments, and various modifications can be made without departing from the spirit and scope of the invention. In addition, the above embodiments are only examples and are not intended to limit the scope of the invention. These new embodiments can be implemented in other various forms, and various omissions, substitutions, and changes can be performed. These embodiments and modifications thereof are included in the scope and spirit of the invention, and are also included in the invention described in the scope of the claims and their equivalents.

For example, a porous metal complex can be used as the porous gas molecule adsorption material. Porous metal complexes are a new concept of substance groups that go beyond boundaries between organic compounds and inorganic compounds by utilizing a metal complex. A "coordination polymer (in particular, a porous coordination polymer (PCP) having a usable space with a nano size or a metal organic framework (MOF)" is receiving focus as a new material.

REFERENCE SIGNS LIST

1 Gas sensor
2 Detection heat sensitive resistive element
2a Compensation heat sensitive resistive element
3 Gas molecule adsorption member
3a Materials having different adsorption properties
4 Base member
5 Exterior case
8 Heating and/or cooling element
10 Gas detection device
10a Detection circuit part
12 Microcomputer
17 Power supply circuit
18 Heating and/or cooling device (temperature control unit)
21 Substrate
22 Conductive layer
22b Lead part
23 Thin film element layer
24 Protective insulating layer
42 Conductive terminal part
51 Ventilation part
Te Thermoelectric element

What is claimed is:

1. A gas sensor, comprising:
a heat sensitive resistive element having at least a pair of electrodes;
a lead part which is electrically connected to the heat sensitive resistive element by welding, while having no inclusions; and
a porous gas molecule adsorption material which is thermally coupled to the heat sensitive resistive element, has a pore, and adsorbs molecules with a diameter smaller than a diameter of the pore, wherein adsorbed specific gas molecules are desorbed by heating to further change a temperature of the porous gas molecule adsorption material due to desorption; and
wherein, during heating of the porous gas molecule adsorption material, an overpower is supplied to the heat sensitive resistive element to put the heat sensitive resistive element into a thermal runaway state.

2. The gas sensor according to claim 1,
wherein the lead part has a thermal conductivity of 5 W/m·K to 25 W/m·K and a cross-sectional area of 0.001 mm$^2$ to 0.03 mm$^2$, and is formed of a weldable material.

3. The gas sensor according to claim 2,
wherein the heat sensitive resistive element is formed by forming a thin film element layer into a film on a substrate, and the substrate has a thickness of 10 μm to 100 μm.

4. The gas sensor according to claim 3,
wherein the porous gas molecule adsorption material is formed into a film on a surface of the heat sensitive resistive element, and a thickness of the formed porous gas molecule adsorption material is 1 μm to 5 μm.

5. The gas sensor according to claim 2,
wherein the porous gas molecule adsorption material is formed into a film on a surface of the heat sensitive resistive element, and a thickness of the formed porous gas molecule adsorption material is 1 μm to 5 μm.

6. The gas sensor according to claim 1,
wherein the heat sensitive resistive element is formed by forming a thin film element layer into a film on a substrate, and the substrate has a thickness of 10 μm to 100 μm.

7. The gas sensor according to claim 6,
wherein the porous gas molecule adsorption material is formed into a film on a surface of the heat sensitive resistive element, and a thickness of the formed porous gas molecule adsorption material is 1 μm to 5 μm.

8. The gas sensor according to claim 1,
wherein the porous gas molecule adsorption material is formed into a film on a surface of the heat sensitive resistive element, and a thickness of the formed porous gas molecule adsorption material is 1 μm to 5 μm.

9. The gas sensor according to claim 1,
wherein the lead part is formed into a foil-like lead frame shape.

10. The gas sensor according to claim 1,
wherein the heat sensitive resistive element is a thermistor.

11. The gas sensor according to claim 1, comprising a heating and/or cooling element which maintains the gas sensor at a constant temperature.

12. The gas sensor according to claim 11,
wherein the heating and/or cooling element is a thermoelectric element.

13. A gas detection device, comprising:
the gas sensor according to claim 1; and
a heating and/or cooling device which maintains the gas sensor at a constant temperature.

14. A gas detection method for a gas sensor comprising a heat sensitive resistive element having at least a pair of electrodes, a lead part which is electrically connected to the heat sensitive resistive element by welding, while having no inclusions, and a porous gas molecule adsorption material which is thermally coupled to the heat sensitive resistive element, has a pore, and adsorbs molecules with a diameter smaller than a diameter of the pore, wherein adsorbed specific gas molecules are desorbed by heating to change a temperature due to desorption, the method comprising:
a step of maintaining the gas sensor at a constant temperature;
a heating step of heating the porous gas molecule adsorption material, wherein, in the heating step, an overpower is supplied to the heat sensitive resistive element to put the heat sensitive resistive element into a thermal runaway state; and a detecting step of detecting a specific gas according to change in an output of the heat sensitive resistive element due to the heating.

15. The gas detection method according to claim 14, wherein, in order to detect the specific gas, an output of a reference gas is measured in advance.

16. The gas detection method according to claim 15, wherein, in the detecting step, a concentration of the specific gas is detected by comparing a measurement result of the output of the reference gas with a measurement result of an output of the specific gas in advance.

17. The gas detection method according to claim 14, wherein the constant temperature is 10° C. or lower.

* * * * *